US012629458B2

(12) United States Patent
Hisatomi et al.

(10) Patent No.: US 12,629,458 B2
(45) Date of Patent: May 19, 2026

(54) AGENT TO BE USED IN INTRAOCULAR MEMBRANE DETACHMENT SURGERY

(71) Applicants: FUKUOKA UNIVERSITY, Fukuoka (JP); SEIKAGAKU CORPORATION, Tokyo (JP)

(72) Inventors: Toshio Hisatomi, Fukuoka (JP); Kiyoshi Suzuki, Tokyo (JP)

(73) Assignees: FUKUOKA UNIVERSITY, Fukuoka (JP); SEIKAGAKU CORPORATION, Tokyo (JP)

( * ) Notice: Subject to any disclaimer, the term of this patent is extended or adjusted under 35 U.S.C. 154(b) by 896 days.

(21) Appl. No.: 17/910,668

(22) PCT Filed: Mar. 24, 2021

(86) PCT No.: PCT/JP2021/012207
§ 371 (c)(1),
(2) Date: Sep. 9, 2022

(87) PCT Pub. No.: WO2021/193707
PCT Pub. Date: Sep. 30, 2021

(65) Prior Publication Data

US 2023/0136938 A1 May 4, 2023

(30) Foreign Application Priority Data

Mar. 25, 2020 (JP) ................................. 2020-054641

(51) Int. Cl.
*A61L 31/14* (2006.01)
*A61F 9/007* (2006.01)
(Continued)

(52) U.S. Cl.
CPC .............. *A61L 31/14* (2013.01); *A61F 9/007* (2013.01); *A61L 31/042* (2013.01); *C08L 5/10* (2013.01)

(58) Field of Classification Search
CPC ....................................................... A61L 31/14
See application file for complete search history.

(56) References Cited

U.S. PATENT DOCUMENTS 5,066,276 A 11/1991 Wang
6,031,017 A * 2/2000 Waki .................... A61L 31/042 522/89
2019/0015559 A1 1/2019 Sakai et al.

FOREIGN PATENT DOCUMENTS

CN 102225220 A 10/2011
JP H02-104352 A 4/1990
JP 2016-172783 A 9/2016
WO WO-97/22371 A1 6/1997
(Continued)

OTHER PUBLICATIONS

European Extended Search Report issued in corresponding European Patent Application No. 21775500.8 dated Apr. 30, 2024 (9 pages).
(Continued)

*Primary Examiner* — Benjamin J Packard
(74) *Attorney, Agent, or Firm* — Foley & Lardner LLP

(57) ABSTRACT

An object of the present invention is to find a useful means for removing an intraocular membrane. The present invention relates to an agent for use in intraocular membrane peeling surgery, which contains a solution containing a hydrogel-forming material and satisfies the following formula 1 with respect to the dynamic viscoelasticity measured at a temperature of 25 to 40° C. and a frequency of 1 Hz.

$$0<V_{max}\leq 3 \quad \text{(Formula 1)}$$

Provided that in the formula 1, $V_{max}$ (Pa/sec) is the maximum change rate of the storage elastic modulus after the initiation of gelation.

19 Claims, 6 Drawing Sheets

(51) Int. Cl.
*A61L 31/04* (2006.01)
*C08L 5/10* (2006.01)

(56) References Cited

FOREIGN PATENT DOCUMENTS

| | | | | | |
|---|---|---|---|---|---|
| WO | WO-2013/170195 | A1 | | 11/2013 | |
| WO | WO-2015002026 | A1 | * | 1/2015 | ........... G08G 1/0129 |
| WO | WO-2017/119296 | A1 | | 7/2017 | |
| WO | WO-2019/108061 | A1 | | 6/2019 | |

OTHER PUBLICATIONS

Nakayama et al., "Viscodelamination for Proliferative Diabetic Retinopathy," Folia ophthalmologica Japonica, vol. 48, 1997, pp. 1050-1053.

Okano et al., "A study of viscodelamination during vitreous surgery for proliferative diabetic retinopathy," Japanese Review of Clinical Ophthalmology, vol. 100, No. 10, 2006, pp. 36-40.

Okano et al., Main Theme I. "Vitreous surgery for diabetic retinopathy. Viscodelamination for fibrovascular membrane with tractional retinal detachment in diabetic retinopathy," Japanese Review of Clinical Ophthalmology, vol. 85, No. 9, 1991, pp. 2408-2413.

Okano, Tadashi, "The Benefits of Viscodelamination in Vitreous Surgery," *Japanese* Journal of ophthalmic surgery, vol. 8, No. 2, 1995, pp. 233-239.

Van Overdam et al., "Vitreous Wiping, a new technique for removal of vitreous cortex remnants during vitrectomy," Acta Ophthalmologica: the ophthalmological journal of the Nordic countries, vol. 97, No. 5, Aug. 1, 2019, pp. e747-e752.

International Searching Authority, "International Search Report," issued in connection with International Patent Application No. PCT/JP2021/012207, dated May 25, 2021.

International Searching Authority, "Written Opinion," issued in connection with International Patent Application No. PCT/JP2021/012207, dated May 25, 2021.

Office Action and Search Report issued in corresponding Chinese Patent Application No. 202180019145.4, dated Mar. 31, 2023.

* cited by examiner

AGENT TO BE USED IN INTRAOCULAR MEMBRANE DETACHMENT SURGERY

CROSS-REFERENCE TO RELATED APPLICATIONS

The present application claims priority under 37 U.S.C. § 371 to International Patent Application No. PCT/JP2021/012207, filed Mar. 24, 2021, which claims priority to and the benefit of Japanese Patent Application No. 2020-054641, filed on Mar. 25, 2020. The contents of these applications are hereby incorporated by reference in their entireties.

TECHNICAL FIELD

The present invention belongs to the field of intraocular membrane peeling surgery.

BACKGROUND ART

Vitreoretinal surgery (hereinafter, also simply referred to as "vitreous surgery") is performed for the purpose of removing a bleeding or vitreous opacity, a membrane-like tissue or a vitreous membrane occurring on the retina, a proliferative membrane formed by proliferating cells in the eye, or the like in various vitreoretinal diseases.

From the viewpoint of preventing the recurrence of the diseases, preventing the induction of new diseases, or the like, more complete removal of a vitreous membrane, a proliferative membrane, or the like remaining on the retina has been demanded, but the removal thereof is often difficult.

Non-Patent Literature 1 describes a technique for removing a vitreous membrane by wiping the vitreous membrane remaining on the retina with forceps equipped with a piece of polyvinyl alcohol (PVA). However, in such a technique, it is difficult to efficiently remove a vitreous membrane. Further, the retina is physically scratched, and therefore, the retina may be damaged.

Patent Literature 1 describes a retina cleaning instrument for cleaning the retina of the eye, which includes a retina cleaning member. The retina cleaning member is configured to remove a vitreous membrane by wiping the retina. The retina cleaning member contains a polymer hydrogel and optionally a crosslinked polymer hydrogel. However, in such a technique, it is difficult to efficiently remove a vitreous membrane in the same manner as in Non-Patent Literature 1. Further, the retina is physically scratched, and therefore, the retina may be damaged.

Non-Patent Literature 2 describes a technique for injecting a viscoelastic liquid between a vitreous membrane or a proliferative membrane and the retina so as to lift the vitreous membrane or the proliferative membrane up from the retina, and excising the vitreous membrane or the proliferative membrane. As the viscoelastic liquid, sodium hyaluronate is used. However, it is difficult to completely lift the vitreous membrane or the proliferative membrane from the retina with such an extremely difficult surgical method, and it is necessary to cut and separate the portion that is not detached by the viscoelastic liquid. Therefore, the operation is complicated, and the retina may be damaged.

Patent Literature 2 describes a crosslinked glycosaminoglycan useful as a therapeutic material for a disease requiring treatment with a long-term residual tissue swelling material such as vesicoureteral reflux. However, Patent Literature 2 does not describe the use of such a crosslinked glycosaminoglycan in intraocular membrane peeling surgery.

Patent Literature 3 describes a crosslinked polymer composition, which contains a first synthetic polymer containing a plurality of nucleophilic groups covalently bonded to a second synthetic polymer containing a plurality of electrophilic groups. The first synthetic polymer is preferably a synthetic polypeptide or polyethylene glycol modified so as to contain a plurality of nucleophilic groups such as primary amino (—$NH_2$) or thiol (—SH) groups. The second synthetic polymer may be a hydrophilic or hydrophobic synthetic polymer containing or derivatized to contain two or more electrophilic groups such as succinimidyl groups. The composition may further contain another component such as a naturally occurring polysaccharide or protein (glycosaminoglycan or collagen, or the like) or a bioactive agent. The crosslinked polymer composition is used as a bioadhesive or the like for tissue adhesion. However, Patent Literature 3 does not describe the use of such a crosslinked polymer composition in intraocular membrane peeling surgery.

CITATION LIST

Patent Literature

Patent Literature 1: WO 2019/108061
Patent Literature 2: JP-A-2016-172783
Patent Literature 3: WO 97/22371

Non-Patent Literature

Non Patent Literature 1: Acta Ophthalmologica 2019: 97: e747-e752
Non-Patent Literature 2: Japanese Review of Clinical Ophthalmology, 85(9): 2408 (1991)

SUMMARY OF INVENTION

As described above, more efficient and convenient removal of the intraocular membrane such as a vitreous membrane or a proliferative membrane remaining on the retina has been demanded. Therefore, the object of the present invention is to find a useful means for removing the intraocular membrane.

The present invention has been conducted in view of the above problem, and in order to solve the above problem, the present inventors have conducted intensive studies on a useful means for peeling the intraocular membrane. As a result, they found a method in which a pharmaceutical agent is injected into the eye to form a hydrogel adhering to the intraocular membrane, and the membrane is peeled together with the hydrogel. In addition, they found a material suitable for such a method. Based on such findings, the present invention has been completed.

That is, the present invention relates to the following.

[1] An agent for use in intraocular membrane peeling surgery, containing a solution containing a hydrogel-forming material, wherein with respect to the dynamic viscoelasticity measured at a temperature of 25 to 40° C. and a frequency of 1 Hz, the following formula 1 is satisfied:

$$0<V_{max}\leq 3 \qquad \text{(Formula 1)}$$

wherein $V_{max}$ (Pa/sec) is the maximum change rate of the storage elastic modulus after the initiation of gelation.

[2] The agent described in [1], wherein the hydrogel-forming material contains a polymer.

[3] The agent described in [2], wherein the polymer contains a compound selected from the group consisting of a polysaccharide derivative, a polyalkylene glycol derivative, a collagen derivative, a polyvinyl alcohol derivative, and fibrinogen.

[4] The agent described in [2], wherein the polymer contains a compound selected from the group consisting of a polysaccharide derivative and a polyalkylene glycol derivative.

[5] The agent described in any one of [1] to [4], wherein the gelation is caused by a crosslinking reaction.

[6] The agent described in any one of [1] to [5], wherein the hydrogel-forming material contains two or more types of compounds.

[7] The agent described in [6], wherein the gelation is initiated by mixing the two or more types of compounds.

[8] The agent described in any one of [1] to [7], wherein the intraocular membrane is at least one selected from the group consisting of a vitreous membrane and a proliferative membrane.

[9] The agent described in any one of [1] to [8], wherein a tensile stress measured using a texture analyzer 3 minutes after the initiation of gelation is $-3\times10^{-4}$ N/mm$^2$ or more.

[10] The agent described in any one of [1] to [9], wherein the agent contains a visualizing agent.

[11] The agent described in any one of [1] to [10], wherein with respect to the dynamic viscoelasticity measured at a temperature of 25 to 40° C. and a frequency of 1 Hz, the following formula 2 is satisfied:

$$0.05 \le V_{max} \le 2 \quad \text{(Formula 2)}$$

wherein $V_{max}$ (Pa/sec) is the same as in the formula 1.

[12] The agent described in any one of [1] to [11], wherein the $V_{max}$ is the maximum change rate of the storage elastic modulus after the initiation of gelation until 900 seconds.

[13] The agent described in any one of [1] to [12], wherein the hydrogel-forming material contains the following glycosaminoglycan derivative A and one selected from the group consisting of the following glycosaminoglycan derivative B and compound C:

(1) a GAG derivative A in which an SPAAC-type reactive group is introduced into a carboxyl group of a glycosaminoglycan via an amide bond and a divalent spacer group;

(2) a glycosaminoglycan derivative B in which a complementary reactive group to the reactive group in (1) is introduced into a carboxyl group via an amide bond and a divalent spacer group; and (3) a compound C defined by the following structure having at least two complementary reactive groups to the reactive group in (1):

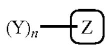

[wherein Y's are the same or different and are each a complementary reactive group to the reactive group in (1); Z is an n-valent spacer group; and n is an integer of 2 or more].

[14] An injector, which is filled with the agent described in any one of [1] to [13].

[15] A method for peeling the intraocular membrane, including applying the agent described in any one of [1] to [13] onto the intraocular membrane of a patient.

[16] The method described in [15], wherein the intraocular membrane is peeled after 10 seconds or more have elapsed from the intraocular administration.

[17] An agent, which contains a solution containing a hydrogel-forming material, wherein the agent is used by being injected into the eye of a patient to form a hydrogel adhering to the intraocular membrane so as to peel the membrane together with the hydrogel.

DESCRIPTION OF EMBODIMENTS

Hereinafter, embodiments of the present invention will be described, but the present invention is not limited only to the following embodiments.

The agent to be used in intraocular membrane peeling surgery of the present invention (hereinafter, also referred to as "the agent according to the present invention") and the method for peeling the intraocular membrane have an excellent effect on removing the intraocular membrane. In addition, the agent according to the present invention and the peeling method are also excellent in convenience as compared with the conventional extremely advanced surgical procedures.

<Agent for use in Intraocular Membrane Peeling Surgery>

One aspect of the present invention relates to an agent for use in intraocular membrane peeling surgery, which contains a solution containing a hydrogel-forming material (hereinafter sometimes referred to as "the hydrogel-forming material of the present invention"), wherein with respect to the dynamic viscoelasticity measured at a temperature of 25 to 40° C. and a frequency of 1 Hz, the following formula 1 is satisfied.

$$0<V_{max}\leq 3 \quad \text{(Formula 1)}$$

Provided that in the formula 1, $V_{max}$ (Pa/sec) is the maximum change rate of the storage elastic modulus after the initiation of gelation.

In the present description, the hydrogel-forming material is a material capable of forming a hydrogel. Further, in the present description, the hydrogel is a gel, which contains water and is poorly soluble or insoluble in water. In the present description, the term "poorly soluble in water" means that when immersed in water for 1 hour or more, almost no dissolution is observed and a shape before immersion is maintained. For example, the solubility of the hydrogel in water may be 1 g/L or less at 20° C.

As described above, as a result of intensive studies, the present inventors have come up with a method in which the intraocular membrane, the remaining of which is problematic in vitreoretinal surgery, is made to adhere to a viscoelastic material, and the intraocular membrane is peeled together with the viscoelastic material. Further, the present inventors have come up with the use of a hydrogel that satisfies the maximum change rate of the storage elastic modulus within the above-mentioned specific range as the viscoelastic material suitable for such a method, and thus completed the present invention.

Figure 1:
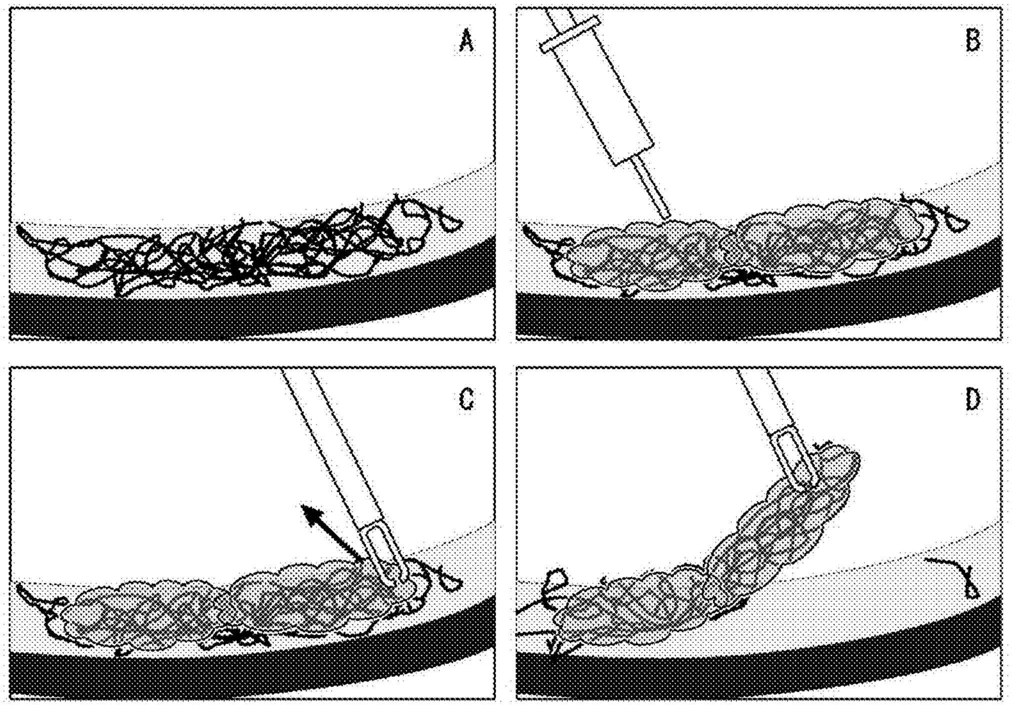
FIG. 1 is a schematic view showing one aspect of a method for peeling the intraocular membrane of the present invention. A of FIG. 1 shows a state where the intraocular membrane adheres to the inner limiting membrane. B of FIG. 1 shows a state where a hydrogel-forming material is injected onto the intraocular membrane. C of FIG. 1 shows a state where a hydrogel is formed on the intraocular membrane. D of FIG. 1 shows a state where a hydrogel that has adhered to the intraocular membrane and gelled is peeled.

One aspect of the method for peeling the intraocular membrane of the present invention will be described with reference to FIG. 1. A of FIG. 1 schematically shows a state where the intraocular membrane, such as the remaining vitreous membrane or the proliferative membrane, in vitreoretinal surgery adheres to the inner limiting membrane corresponding to the retinal surface. The remaining vitreous membrane or the proliferative membrane formed by cell proliferation tends to shrink, which may cause retinal detachment or the like. Therefore, it is necessary to peel and remove the intraocular membrane such as the remaining vitreous membrane or the proliferative membrane, or the like. In one aspect of the present invention, as shown in B of FIG. 1, the hydrogel-forming material contained in an agent according to the present invention is injected onto the intraocular membrane. The hydrogel-forming material is in the form of a solution, and therefore can be easily injected into the vitreous cavity. As shown in C of FIG. 1, a hydrogel is formed on the intraocular membrane. As shown in D of FIG. 1, the operation is performed so that the hydrogel that has adhered to the vitreous membrane and gelled is grasped and peeled. In this manner, the intraocular membrane can be efficiently and easily peeled. As described above, the present invention effectively assists the manipulation of a surgeon during the intraocular membrane peeling surgery in the eye, which is a small space.

<<Maximum Change Rate of Storage Elastic Modulus>>

The agent according to the present invention contains a solution containing a specific hydrogel-forming material, and the agent according to the present invention forms a hydrogel that satisfies the maximum change rate of the storage elastic modulus within the above-mentioned specific range after the initiation of gelation and is suitable for the method for peeling the intraocular membrane.

From the viewpoint of adhesiveness to the intraocular membrane, ease of grasping and peeling the hydrogel incorporated with the intraocular membrane, ease of handling such as passability through a needle or the like for intraocular administration and rapid gelation, or the like, the maximum change rate of the storage elastic modulus $V_{max}$ after the initiation of gelation of the agent according to the present invention is more than 0 Pa/sec and 3 Pa/sec or less. The $V_{max}$ may be preferably, for example, 0.01 Pa/sec or more, 0.05 Pa/sec or more, 0.3 Pa/sec or more, 0.4 Pa/sec or more, or 0.6 Pa/sec or more, and may be 2 Pa/sec or less, 1.5 Pa/sec or less, 1.0 Pa/sec or less, or 0.8 Pa/sec or less, and may be any consistent combination thereof.

The change ratio of the storage elastic modulus as used herein is a change ratio (Pa/sec) of the storage elastic modulus G' (Pa) per unit time (sec) obtained from the measurement result of the dynamic viscoelasticity.

Further, the maximum change rate of the storage elastic modulus as used herein refers to the maximum change rate of the storage elastic modulus during a time range until the storage elastic modulus turns from increase to plateau or decrease. That is, the maximum change rate of the storage elastic modulus $V_{max}$ is the maximum value of the slope of a tangent (dG'/dt) of a time course curve prepared with the vertical axis representing the storage elastic modulus G' and the horizontal axis representing the time t. For example, the storage elastic modulus of a crosslinked material in a crosslinking reaction increases in proportion to the crosslinking density, and the maximum change rate of the storage elastic modulus can be regarded as a value representative of the change ratio of the storage elastic modulus within a predetermined time range after the initiation of gelation by a crosslinking reaction.

In order to use the agent according to the present invention suitably in vitreous surgery, the time range may be, for example, up to 900 seconds, up to 600 seconds, up to 300 seconds, up to 180 seconds, up to 100 seconds, or up to 60 seconds from the initiation of gelation (more than 0 seconds after the initiation of gelation), or may be any consistent combination thereof.

The storage elastic modulus G' (Pa) in the present invention is a value measured based on a conventional measurement method for dynamic viscoelasticity. Specifically, for example, as a dynamic viscoelasticity measuring device, a rheometer equipped with parallel plates at a plate interval of 0.5 mm is used, and an agent for intraocular membrane peeling surgery after the initiation of gelation is used as a sample, and a value measured at a frequency of 1 Hz and any temperature from 25 to 40° C. (preferably 25° C.) can be used.

The maximum change rate of the storage elastic modulus of the agent according to the present invention can be controlled by, for example, a means for adjusting the concentration of the hydrogel-forming material in the solution containing the hydrogel-forming material, or adjusting the ratio of the hydrogel-forming material to a crosslinking agent when the crosslinking agent is used, or the like. More specifically, the maximum change rate of the storage elastic modulus can be increased, for example, by increasing the concentration of the hydrogel-forming material in the solution containing the hydrogel-forming material.

<<Tensile Stress>>

The agent according to the present invention preferably has appropriate ductility from the viewpoint of adhesiveness to the intraocular membrane, ease of grasping and peeling the hydrogel incorporated with the intraocular membrane, or the like. In one embodiment, the ductility of the agent according to the present invention expressed in terms of tensile stress 3 minutes after the initiation of gelation may be, for example, $-3\times10^{-4}$ N/mm$^2$ or more, $-2\times10^{-4}$ N/mm$^2$ or more, or $-1.5\times10^{-4}$ N/mm$^2$ or more, and may be $-0.1\times10^{-4}$ N/mm$^2$ or less, $-0.5\times10^{-4}$ N/mm$^2$, or $-0.6\times10^{-4}$ N/mm$^2$ or less, and may be any consistent combination thereof.

The tensile stress in the present invention is a value measured based on a conventional measurement method for tensile stress. Specifically, for example, a measurement method based on Ippei Watanabe et al., Chem. Pharm. Bull. 67 (3), 277-283 (2019) can be adopted. More specifically, for example, a texture analyzer is used as a tensile stress tester, and a value measured at any temperature from 20° C. to 25° C. (preferably 25° C.) using an agent for intraocular membrane peeling surgery at 3 minutes after the initiation of gelation as a sample liquid.

The tensile stress of the agent according to the present invention can be controlled, for example, by selecting the type of hydrogel-forming material, or the like.

<<Hydrogel-Forming Material>>

The hydrogel-forming material can be used without particular limitation as long as it can form a hydrogel that satisfies the maximum change rate of the storage elastic modulus within the above-mentioned specific range. In one embodiment, the hydrogel-forming material contains a polymer. The polymer is not particularly limited, and for example, a derivative in which a reactive functional group or the like is introduced into a compound selected from the group consisting of a polysaccharide, a polyalkylene glycol, collagen, polyvinyl alcohol, and the like, as a basic skeleton, fibrinogen, and the like can be exemplified, and the polymer is preferably a polysaccharide or a polyalkylene glycol. As the hydrogel-forming material, one type can be used or two or more types can be used in combination. From the viewpoint of handleability in vitreous surgery, the hydrogel-forming material preferably contains a polysaccharide, and more preferably contains a glycosaminoglycan (GAG) described later.

Examples of the polysaccharide can include, but are not limited to, glycosaminoglycans (GAGs) such as hyaluronic acid, alginic acid, celluloses, dextrans, chitosan, and medically acceptable salts thereof.

The glycosaminoglycan is an acidic polysaccharide having a repeating structural unit of a disaccharide composed of an amino sugar (glucosamine or galactosamine) and uronic acid or galactose. Examples of such GAG include hyaluronic acid, heparin, heparan sulfate, and keratan sulfate. In the present invention, hyaluronic acid is particularly preferred among these.

In the present invention, the origin of alginic acid is not particularly limited.

As the cellulose, a known one can be used, and examples thereof include cellulose and carboxymethyl cellulose. In the present invention, the origin of the cellulose is not particularly limited.

As the dextran, a known one can be used, and examples thereof include carboxymethyl dextran. In the present invention, the origin of the dextran is not particularly limited.

In the present invention, the origin of the chitosan is not particularly limited. In the present invention, the degree of deacetylation of the chitosan is not particularly limited, but can be, for example, 70 to 100%.

Examples of medically acceptable salt include alkali metal salts such as a sodium salt and a potassium salt, and alkaline earth metal salts such as a magnesium salt and a calcium salt.

Examples of the polyalkylene glycol include, but are not limited to, one in which the number of carbon atoms of an alkylene group that is a constituent unit of the polyalkylene glycol is, for example, 2 to 4, preferably 2 or 3, and more preferably 2. Specific examples thereof include polyethylene glycol, polypropylene glycol, and polybutylene glycol. Preferred examples of the polyalkylene glycol include polyethylene glycol. Further, as the polyalkylene glycol, one having a multi-branched polyalkylene glycol structure can also be used.

Collagen is a protein that mainly constitutes the dermis, ligament, tendon, bone, cartilage, etc. of a vertebrate, and examples thereof include type I to type XIX, and any of them can be used. In the present invention, the origin of collagen is not particularly limited.

Examples of the polyvinyl alcohol include, but are not limited to, polyvinyl acetate alcohol, polyvinyl formate alcohol, polyvinyl benzoate alcohol, polyvinyl stearate alcohol, polyvinyl chloroacetate alcohol, polyvinyl fluoroacetate alcohol, and polyvinyl propionate alcohol. Preferred examples of the polyvinyl alcohol include polyvinyl acetate alcohol. Further, as the polyvinyl alcohol, one having a multi-branched polyvinyl alcohol structure can also be used.

The fibrinogen is a protein involved in blood coagulation. A preparation (fibrin glue) in which a glue-like clot formed by the action of thrombin, which is an enzyme, on fibrinogen is used for tissue closure, adhesion of a damaged part of an organ, hemostasis, or the like is commercially available.

The type of fibrinogen is not particularly limited, and it may be derived from blood or may be produced by a recombination technique. A commercially available fibrin glue can also be used. Examples of the commercially available fibrin glue used in the present invention can include, but are not limited to, BOLHEAL (manufactured by KM Biologics Co., Ltd.), Tisseel (manufactured by Baxter International, Inc.), and Beriplast (manufactured by CSL Behring LLC).

The derivative in the present description may be a derivative derivatized so that a hydrogel is allowed to form.

The hydrogel-forming material of the present invention may form a hydrogel using a reactive functional group originally possessed by the material, and may be a derivative into which a reactive functional group allowing it to form a hydrogel is introduced.

The derivative derivatized so that a hydrogel is allowed to form is not limited to but may be, for example, one having a reactive functional group. The reactive functional group is not particularly limited, and may be one that causes gelation. Examples thereof include electrophilic functional groups and nucleophilic functional groups such as a carbodiimide group, a carbonylimidazole group, a sulfonyl chloride group, a chlorocarbonate group, an N-hydroxysuccinimidyl ester group, a succinimidyl ester group, a sulfosuccinimidyl ester group, an N-hydroxyethoxylated succinimide ester group, a methanediisocyanate group, a methylene-bis(4-cyclohexylisocyanate) group, an isocyanate group, a diisocyanate group, a hexamethylene diisocyanate group, a maleimide group, an alkynyl group, an alkynylene group, a vinyl group, an acryloyl group, a methacryloyl group, an amino group, a hydroxy group, a carboxy group, a thiol group, an azide group, and a hydrazide group. The selection, introduction, or the like of the reactive functional group can be performed based on a conventionally known method. For example, the degree of substitution with the reactive functional group in a polysaccharide derivative (a value expressing the number of substituents with respect to the number of repeating units as a percentage) is usually 1 to 60%, and preferably 5 to 40%.

The molecular weight of the hydrogel-forming material used in the present invention is not particularly limited as long as it can form a hydrogel that satisfies the maximum change rate of the storage elastic modulus within the above-mentioned specific range, and for example, one having a weight average molecular weight of about 500 to 10,000,000 can be used. Note that the molecular weight of the hydrogel-forming material in the present description is a value determined using gel permeation chromatography (GPC).

The agent according to the present invention includes both embodiment (1) in which the hydrogel-forming material is previously contained in a container in the form of a solution, and embodiment (2) in which the hydrogel-forming material contained in a container is in a dry state and is dissolved in a solvent upon use.

The solvent used in the solution containing the hydrogel-forming material is not particularly limited, and for example, water, an intraocular irrigating solution (BSS), phosphate buffered saline (PBS), or the like can be used.

The concentration of the hydrogel-forming material in the solution containing the hydrogel-forming material is not particularly limited, but is, for example, 0.2 wt % or more, 0.8 wt % or more, 0.9 wt % or more, or 1.0 wt % or more, and may be 10 wt % or less, 3 wt % or less, 2 wt % or less, or 1.5 wt % or less, and may be any consistent combination thereof.

<<Gelation>>

In general, the initiation point of gelation is recognized as a time point when in the measurement of the dynamic viscoelasticity, the relationship between the storage elastic modulus G' (Pa) and the loss elastic modulus G" (Pa) changes from G' G" to G"<G'.

A method for forming a hydrogel with the hydrogel-forming material is not limited, but may be, for example, one in which a three-dimensional network structure is formed and gelled by crosslinks formed between the hydrogel-forming materials. In a preferred embodiment of the present invention, the hydrogel-forming material that is gelled by a crosslinking reaction is used.

The agent according to the present invention may contain a solution containing a compound that is one type of hydrogel-forming material, or may contain a plurality of solutions each containing any of two or more types of compounds that are hydrogel-forming materials in a combination. In one embodiment, if it is a combination of two types of compounds which are hydrogel-forming materials, the agent may contain a solution (1) containing one of the compounds in the combination and a solution (2) containing the other compound in the combination.

In one embodiment, the combination is a combination of compounds into which functional groups that are paired to form a crosslinked structure (hereinafter, sometimes referred to as "a reactive functional group and a complementary reactive functional group to the reactive functional group") are separately introduced, and a hydrogel is formed by a crosslinking reaction between the functional groups.

In one embodiment, the hydrogel-forming material having a reactive functional group and a compound having a complementary reactive functional group to the reactive functional group are contained in separate containers. In a more specific embodiment, the compound having the complementary reactive functional group is also a hydrogel-forming material.

When two or more types of compounds are used in the agent according to the present invention, for example, the agent may contain a combination of a hydrogel-forming material having a reactive functional group and a hydrogel-forming material having a complementary reactive functional group to the reactive functional group, or may contain a combination of a hydrogel-forming material having a reactive functional group and a crosslinking agent.

When two or more types of compounds are used as the hydrogel-forming materials, for example, the gelation may be initiated by mixing the two or more types of compounds.

When two or more types of compounds are used, the blending amount thereof can be appropriately selected depending on the type of reactive functional group, the performance of the target hydrogel, or the like, and the compounds can be blended so that the reactive functional group and the complementary reactive functional group to the reactive functional group are present at a molar ratio of 4:1 to 1:4, 2:1 to 1:2, or 1:1.

The solution (1) contains one of the compounds in the combination and the solution (2) contains the other compound in the combination, but each solution may further contain another combination of materials that form a hydrogel. That is, in addition to a single-solute solution form in which one solution contains one material, a multi-solute solution form in which one solution contains two or more solutes can also be used as the solution in the present invention unless an undesired phenomenon occurs in one solution.

Further, in this aspect, the solution (1) containing one compound of at least two types of compounds that form a hydrogel in the combination and the solution (2) containing the other compound are used, but it is not meant to use these only two types of solutions. Therefore, solutions containing another combination of compounds that form a hydrogel may be additionally used unless the formation of the hydrogel is impaired.

That is, the combination of solutions may be one or more, and an embodiment in which solutions that are different from the solution (1) and the solution (2), and contain compounds in a combination different from the combination contained in the solution (1) and the solution (2) are used together with the solutions (1) and (2) is also included in this aspect.

The different two types of functional groups that are paired to form a crosslinked structure are not limited, and a preferred example is a combination of functional groups that cause a click reaction, or the like, and for example, a combination of an azide and an alkyne (azide-alkyne cycloaddition (Huisgen cycloaddition)) or the like can be exemplified.

As one of the hydrogels, which is a combination of functional groups that cause such a click reaction and can be used in the present invention, a crosslinked GAG obtained by subjecting a derivative in which an SPAAC (strain-promoted azide-alkyne cycloaddition)-type reactive (functional) group is introduced into a GAG such as hyaluronic acid to an SPAAC reaction described in JP-A-2016-172783 is exemplified. The gelation can be performed by regulating the properties of the solutions containing each derivative and mixing the solutions, according to the teaching of JP-A-2016-172783.

More specifically, one of the hydrogels that can be used in the present invention is composed of the following crosslinked product.

A crosslinked GAG in which the following group:

—CONH—$R^1$—X—$R^2$—NHCO—, or

—CONH—$R^3$—X—$R^4$—X'—$R^5$—NHCO—

[wherein —CONH and NHCO— at both ends mean an amide bond via a carboxyl group of a GAG molecule, $R^1$, $R^2$, $R^3$, $R^4$, and $R^5$ are the same or different and represent an alkylene group, an alkenylene group, or an alkynylene group, and —$CH_2$— in the group may be substituted with >C═O (that is, —C(═O)—), —CONH—, arylene, —O—, or —S—;

X and X' are the same or different and represent a structure represented by the formula:

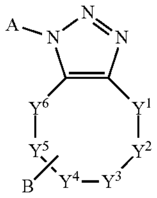

the direction of the bond A or B may be either direction; here, A and B represent a binding site;

$Y^1$, $Y^2$, $Y^3$, $Y^4$, $Y^5$, and $Y^6$ are the same or different and represent —$CR^6R^{6'}$—, —C(—$R^6$)═, —$NR^7$—, ═N—, —O—, or —S—, and —$NR^7$—, ═N—, —O—, and —S— are not adjacent to each other;

$R^6$ and $R^{6'}$ are the same or different and represent a hydrogen atom, a halogen atom, a hydroxyl group, an amino group which may be mono- or di-substituted with an alkyl group, an alkyl group, an alkenyl group, an alkynyl group, an alkoxy group, or a carboxyl group, or may be joined to form an oxo group, and —$CH_2$— in the alkyl group, alkenyl group, alkynyl group, or alkoxy group may be substituted with >C═O, —CONH—, arylene, —O—, or —S—; and $R^7$ represents an alkyl group, an alkenyl group, or an alkynyl group, and —$CH_2$— in the alkyl group, alkenyl group, or alkynyl group may be substituted with >C═O, —CONH—, arylene, —O—, or —S—; or in two neighboring groups of $Y^1$, $Y^2$, $Y^3$, $Y^4$, $Y^5$, and $Y^6$, $R^6$ and $R^{6'}$ can be joined together with a ring atom bound thereto to form a saturated or unsaturated 3- to 6-membered ring, and the bond B can also bind to the 3- to 6-membered ring]

is bound between a carboxyl group of a first GAG molecule and a carboxyl group of a second GAG molecule via an amide bond (the first GAG molecule and the second GAG molecule may be the same molecule).

As one aspect of the crosslinked GAG, a crosslinked GAG, which has, as a basic skeleton, a repeating structure of a structural unit represented by the formula:

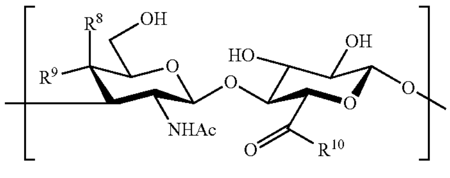

[wherein $R^8$ and $R^9$ represent a hydrogen atom or a hydroxyl group; but when $R^8$ is a hydroxyl group, $R^9$ is a hydrogen atom, and when $R^8$ is a hydrogen atom, $R^9$ is a hydroxyl group;

$R^{10}$ represents $R^{11}$ or the crosslink described above; and $R^{11}$ is ONa or OH], and when $R^8$ is a hydroxyl group, at least one of the hydroxyl groups in the structural unit is —$OSO_3Na$ or —$OSO_3H$ can be preferably exemplified.

The agent according to the present invention may contain, as the hydrogel-forming material, the following (1) GAG derivative A, and one selected from the group consisting of the following (2) GAG derivative B and (3) compound C:

(1) a GAG derivative A in which an SPAAC-type reactive group is introduced into a carboxyl group of a GAG via an amide bond and a divalent spacer group;

(2) a GAG derivative B in which a complementary reactive group to the reactive group in (1) is introduced into a carboxyl group via an amide bond and a divalent spacer group; and (3) a compound C defined by the following structure having at least two complementary reactive groups to the reactive group in (1):

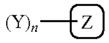

[wherein

Y's are the same or different and are each a complementary reactive group to the reactive group in (1);

Z is an n-valent spacer group; and n is an integer of 2 or more]. That is, the agent according to one embodiment of the present invention contains a combination of (1) the GAG derivative A and (2) the GAG derivative B; or a combination of (1) the GAG derivative A and (3) the compound C.

In the GAG derivatives A and B that constitute the agent according to the present invention, an SPAAC-type reactive group or a complementary reactive group to the reactive group is amide-bonded to a carboxyl group of a GAG via a divalent spacer group. As the divalent spacer group, any chain group can be used unless it is one that inhibits the reaction between the SPAAC-type reactive group and the complementary reactive group to the reactive group. As such a divalent spacer group, the groups $R^1$, $R^2$, $R^3$, $R^4$, and $R^5$ used in the above crosslinked GAG, that is, an alkylene group, an alkenylene group, or an alkynylene group can be used, and —$CH_2$— in the group may be substituted with >C═O, —CONH—, arylene, —O—, or —S—.

The n-valent spacer possessed by the compound C that constitutes the agent according to the present invention is also the same as the divalent spacer, and an n-valent group derived from an alkyl group, an alkenyl group, or an alkynyl group can be used, and —$CH_2$— in the group may be substituted with >C═O, —CONH—, arylene, —O—, or —S—. Here, as the arylene, a phenylene group such as 1,2-, 1,3-, or 1,4-phenylene can be used, and among them, a 1,4-phenylene group can be preferably used. Here, n is an integer of 2 or more, but is preferably 2.

In the agent according to the present invention, the GAG derivatives A and B and the compound C have an SPAAC-type reactive group or a complementary reactive group to the reactive group. The SPAAC-type reaction refers to a reaction using a cycloalkynylenyl group as an alkyne group in a click-type reaction in which an azide group and an alkyne group are reacted to form a 1,2,3-triazole ring. The click-type reaction enables the formation of a 1,2,3-triazole ring quickly, easily, and efficiently without producing undesired by-products. By using a cycloalkynylenyl group as an alkyne group, a crosslinking reaction proceeds promptly and highly selectively due to distortion of the ring structure without a copper catalyst. The GAG derivatives A and B and the compound C that can be adopted in the agent according to the present invention can have an arbitrary SPAAC-type reactive group or a complementary reactive group to the reactive group. As the SPAAC-type reactive group or the complementary reactive group to the reactive group, specifically, a combination of a group derived from a cycloalkynylenyl group having 7 to 9 carbon atoms, preferably 7 or 8 carbon atoms, and more preferably 8 carbon atoms, and an azide group can be used. As the cycloalkynylenyl group, a cyclic group represented by the formula:

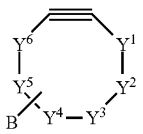

[wherein

B represents a binding site to a spacer group (for example, a divalent spacer group);

$Y^1$, $Y^2$, $Y^3$, $Y^4$, $Y^5$, and $Y^6$ are the same or different and represent —$CR^6R^{6'}$—, —C(—$R^6$)=, —$NR^7$—, =N—, —O—, or —S—, and —$NR^7$—, =N—, —O—, and —S— are not adjacent to each other;

$R^6$ and $R^{6'}$ are the same or different and represent a hydrogen atom, a halogen atom, a hydroxyl group, an amino group which may be mono- or di-substituted with an alkyl group, an alkenyl group, an alkynyl group, an alkoxy group, or a carboxyl group, or may be joined to form an oxo group, and —$CH_2$— in the alkyl group, alkenyl group, alkynyl group, or alkoxy group may be substituted with >C=O, —CONH—, arylene, —O—, or —S—; and $R^7$ represents an alkyl group, an alkenyl group, or an alkynyl group, and —$CH_2$— in the alkyl group, alkenyl group, or alkynyl group may be substituted with >C=O, —CONH—, arylene, —O—, or —S—; or in two adjacent groups of $Y^1$, $Y^2$, $Y^3$, $Y^4$, $Y^5$, and $Y^6$, $R^6$ and $R^{6'}$ can be joined together with a ring atom bound thereto to form a saturated or unsaturated 3- to 6-membered ring, and the bond B can also bind to the 3- to 6-membered ring]

can be exemplified. As such a 3- to 6-membered ring, a 3- to 6-membered cycloalkyl ring or phenyl ring, a 5- to 6-membered heteroaryl ring, and the like can be exemplified.

As a specific example of such a SPAAC-type reactive group or a complementary reactive group to the reactive group, a combination of a reactive group having the following skeleton and an azide group can be preferably exemplified.

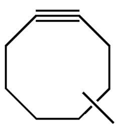
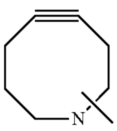
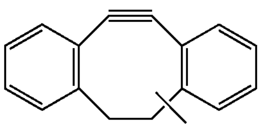
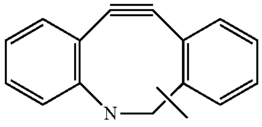
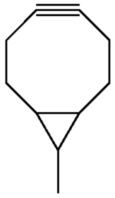

Further, more preferably, a combination of the following group and an azide group can be more preferably exemplified.

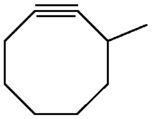
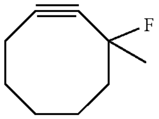
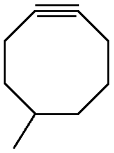
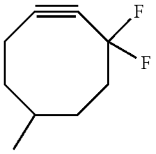
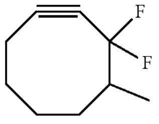
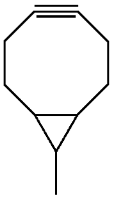
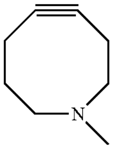
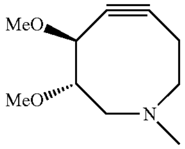
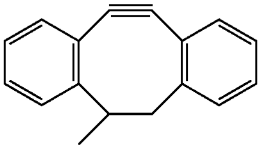
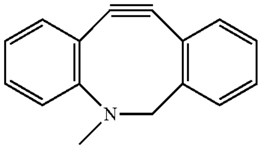
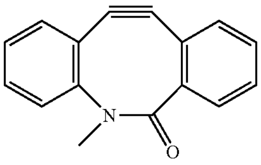

Among the GAG derivatives A and B, as the GAG derivative having a cycloalkynylenyl group as the SPAAC-type reactive group, a GAG derivative in which an amino group of a cyclooctyne derivative amine selected from the following:

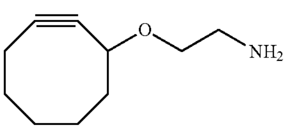
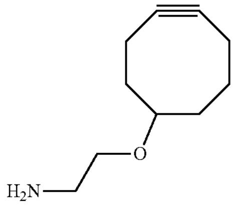
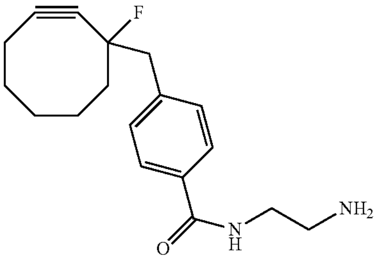
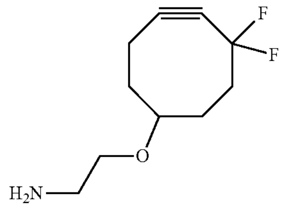

-continued

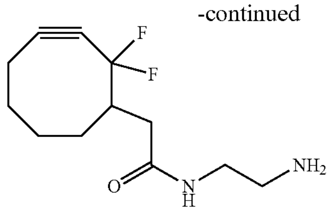

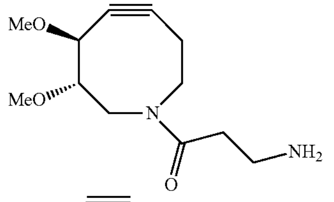

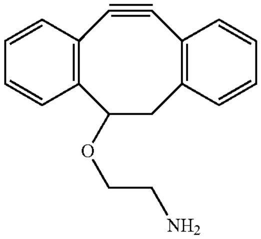

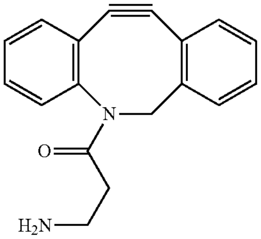

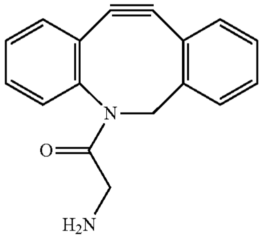

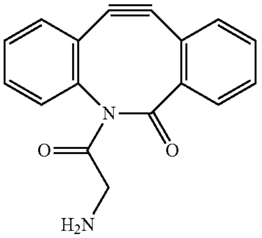

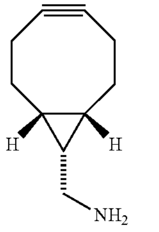

and a carboxyl group of GAG are amide-bonded can be preferably exemplified.

Further, among the GAG derivatives A and B, as the GAG derivative having an azide group as the SPAAC-type reactive group, a GAG derivative obtained by condensation reaction between an amino group of an azide amine selected from the following:

$N_3$—$CH_2$—$CH_2$—$NH_2$;

$N_3$—$CH_2$-$CH_2$-$CH_2$—$NH_2$;

$N_3$—$CH_2$—$CH_2$—$CH_2$—$CH_2$—$NH_2$;

$N_3$—$CH_2$-C(═O)—NH—$CH_2$—$CH_2$—$NH_2$;

$N_3$—$CH_2$—$CH_2$—O—$CH_2$—$CH_2$—$NH_2$; and $N_3$—$CH_2$—[$CH_2$-O—$CH_2$]$_{2-10}$—$CH_2$—$NH_2$;

and a carboxyl group of the GAG can be preferably exemplified.

Further, as the compound C, the following compounds can be preferably exemplified.

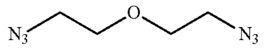

-continued

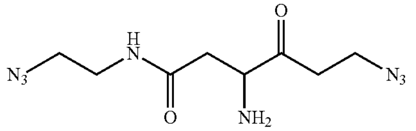

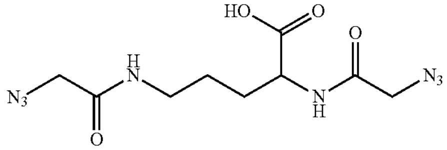

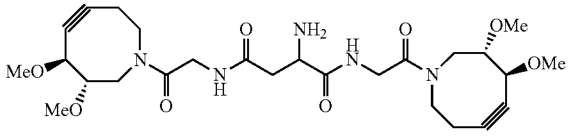

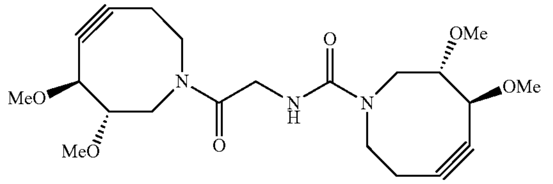

In the agent according to the present invention, the SPAAC-type reactive group and the complementary reactive group to the reactive group possessed by the GAG derivatives A and B and the compound C are present at a molar ratio of 1:1 to 1:4, and preferably at a molar ratio of 1:1.

Another hydrogel that can be used in the present invention is a gel obtained by binding a first synthetic polymer containing a plurality of nucleophilic groups such as primary amino (—$NH_2$) or thiol (—SH) groups and a second synthetic polymer containing a plurality of electrophilic groups such as succinimidyl groups described in WO 97/22371. The gelation can be performed by regulating the properties of the solutions containing each derivative and mixing the solutions according to the teaching of WO 97/22371.

Another hydrogel that can be used in the present invention is a hydrogel composed of a combination of a multi-branched polyalkylene glycol (Multi-arm-PEG) derivative, preferably a multi-branched polyethylene glycol (PEG) derivative containing an N-hydroxysuccinimidyl ester group and a compound containing a complementary reactive functional group to the N-hydroxysuccinimidyl ester group. The multi-branched PEG derivative is a compound in which a plurality of PEG derivatives having a reactive functional group are bound to an end on the side opposite to the reactive functional group. As the compound containing a multi-branched polyalkylene glycol derivative and a complementary reactive functional group to the N-hydroxysuccinimidyl ester group, for example, a commercially available compound can be used.

Note that there are no special restrictions on the number of PEG branches and the type of substituent. Therefore, a structure that is not found in a commercially available multi-branched PEG derivative, for example, an 8-branched PEG derivative having a maleimide group or a 6-branched PEG derivative having a thiol group, or the like can be arbitrarily prepared in accordance with a method for synthesizing a commercially available multi-branched PEG derivative, and such a multi-branched PEG derivative can also be used in the present invention.

Another hydrogel that can be used in the present invention is a hydrogel composed of a combination of a hyaluronic acid derivative containing a thiol group and a compound containing a complementary reactive functional group to the thiol group. As the hyaluronic acid derivative containing a thiol group and the compound containing a complementary reactive functional group to the thiol group, for example, commercially available compounds can be used.

<<Target>>

As a target for which the agent according to the present invention is used, any animal that can suffer from an eye disease, for example, a human and a non-human animal (for example, a dog, a cat, a rabbit, a rat, a mouse, etc.) are exemplified.

The vitreous surgery in the present invention means surgery to peel the intraocular membrane for treating and preventing an eye disease, and preventing the recurrence of an eye disease. Here, examples of the intraocular membrane include a vitreous membrane and a proliferative membrane.

Examples of the eye disease include, but are not limited to, retinal detachment, diabetic retinopathy, proliferative vitreoretinopathy, proliferative diabetic retinopathy, and macular diseases (macular hole, premacular membrane, vitreomacular traction syndrome, macula edema, and age-related macular degeneration).

The dose of the agent according to the present invention varies depending on the symptoms, particularly the condition of the eye, and the age of a patient to whom the agent is administered, the administration method, etc., and may be such an amount that the intraocular membrane can be visually recognized when the agent for intraocular membrane peeling surgery is administered to the vitreous cavity. Although the dose is not limited, for example, in the case of the agent for use in intraocular membrane peeling surgery, generally a dose of 1 to 100 mg at the time of vitreous surgery is exemplified.

<<Visualizing Agent>>

The agent according to the present invention may further contain an agent for visualizing the vitreous body, which is an auxiliary agent at the time of vitreous surgery in addition to the above components. The visualizing agent assists in peeling of the intraocular membrane by visualizing the vitreous body in a method for peeling the intraocular membrane using the agent according to the present invention.

The visualizing agent is not particularly limited as long as it is one used as an auxiliary agent at the time of vitreous surgery, and examples thereof include a pigment such as Brilliant Blue G and triamcinolone acetonide. As for application or the like, it can be applied with reference to a method used in vitreous surgery.

<Injector>

One aspect of the present invention is an agent for use in intraocular membrane peeling surgery according to the present invention, wherein the agent after the initiation of gelation is injectable.

Further, another aspect of the present invention relates to an injector filled with the agent according to the present invention (hereinafter sometimes referred to as "the injector of the present invention"). Note that the matters described for the above-mentioned agent for use in intraocular membrane peeling surgery are all applied to the description of the injector of the present invention.

Since the agent according to the present invention is an agent favorably used for intraocular membrane peeling surgery by being administered to the vitreous cavity in vitreous surgery, the administration form is desirably injection administration, particularly local administration by injection.

For example, in the injector of the present invention, the agent according to the present invention is stored in a syringe chamber, and a plunger is connected to the one end of the syringe chamber. On the other end of the syringe chamber, the injector has a discharge port for the agent for intraocular membrane peeling surgery. The discharge port may be provided with a connecting portion for connecting an injection needle.

Note that the material of the syringe is not limited as long as the material can stably hold the solution containing the hydrogel-forming material, and a glass, a polyolefin-based plastic such as polyethylene or polypropylene, a plastic such as polyethylene terephthalate or polycarbonate, or the like, each of which has excellent visibility can be applied.

In the case where gelation is initiated by mixing two or more types of compounds, as the injector of the present invention, an injector, in which two or more types of chambers are included in a syringe, and the agent according to the present invention is stored in each chamber, and when the plunger is moved forward, two or more types of compounds are mixed so as to enable mixing to form a hydrogel is preferably used.

In one embodiment, a solution containing a hydrogel-forming material having a reactive functional group and a solution containing a compound having a complementary reactive functional group to the reactive functional group are contained in separate syringe chambers. In a more specific embodiment, the compound having the complementary reactive functional group is also a hydrogel-forming material. In a further embodiment, two or more types of solutions contained in separate syringe chambers are mixed at the discharge port provided on one proximal end side of the syringe chamber, and gelation is initiated by the mixing.

The injection needle is not limited as long as it can discharge the hydrogel, but for example, a 25 G to 27 G injection needle can be applied.

<Method for Peeling Intraocular Membrane>

One aspect of the present invention relates to a method for peeling the intraocular membrane including applying the agent according to the present invention onto the intraocular membrane of a patient (hereinafter sometimes referred to as "the method for peeling the intraocular membrane of the present invention"). Note that the matters described for the above-mentioned agent for use in intraocular membrane peeling surgery and injector are all applied to the description of the method for peeling the intraocular membrane of the present invention.

Further, another preferred embodiment of the present invention is a method for peeling the intraocular membrane further including peeling the intraocular membrane. In the method for peeling the intraocular membrane, an intraocular membrane peeling method in conventionally known vitreous surgery can be used except that a hydrogel is used. By using the agent according to the present invention, the intraocular membrane to which the hydrogel has adhered is peeled, and therefore, as compared with the case where the intraocular membrane is peeled alone, the intraocular membrane can be efficiently peeled.

Although not limited, the intraocular membrane can be peeled, for example, after 10 seconds or more, 20 seconds or more, or 30 seconds or more have elapsed from the intraocular administration of the agent according to the present invention from the viewpoint of handleability or the like. The peeling of the intraocular membrane may be performed, for example, within 1 hour, within 30 minutes, or within 15 minutes from the intraocular administration of the agent according to the present invention.

EXAMPLES

Hereinafter, preferred embodiments of the present invention will be described in more detail with reference to Examples, but the technical scope of the present invention is not limited to the following Examples.

Example 1

1-1. Preparation of Hydrogel-Forming Material

A two-liquid mixing-type hydrogel-forming material was prepared in accordance with the method described in JP-A-2016-172783. A specific method is shown below.

A 50% (v/v) ethanol aqueous solution of sodium hyaluronate (weight average molecular weight: about 300,000) was prepared (final concentration of sodium hyaluronate: 5 mg/mL, HA reaction solution).

A 0.5 M hydrochloric acid/ethanol (1:1 (v/v)) mixed solution of dibenzocyclooctyne-amine (DBCO-amine) was prepared (final concentration of DBCO-amine: 0.12 mmol/g, DBCO-amine solution). To the HA reaction solution (60 mL), 1 mL of the DBCO-amine solution was added in the presence of a condensation agent (4-(4,6-dimethoxy-1,3,5-triazin-2-yl)-4-methylmorpholinium chloride; DMT-MM). After the reaction solution was stirred overnight at 25° C., the pH was adjusted to 11 or higher with an aqueous sodium hydroxide solution to stop the reaction. Further, the pH of the reaction solution was adjusted to 6 to 7 with an aqueous acetic acid solution. 1.5 g of sodium chloride and 90 mL of ethanol were added to the reaction solution to precipitate the product. After removing the supernatant, the precipitate was washed with ethanol for 3 times. The obtained precipitate was dried, whereby HA-DBCO (hydrogel-forming material 1) was obtained.

A 50% (v/v) aqueous ethanol solution of 2-azidoethylamine hydrochloride (AEA) was prepared (final concentration of AEA: 0.12 mmol/g, AEA solution). To the HA reaction solution (60 mL), 1 mL of the AEA solution was added in the presence of a condensation agent (DMT-MM). Thereafter, the same treatment as the above-mentioned method for preparing HA-DBCO was performed, whereby HA-AEA (hydrogel-forming material 2) was obtained.

1-2. Measurement of Dynamic Viscoelasticity

HA-DBCO solutions and HA-AEA solutions prepared at various concentrations were prepared using BSS Plus 500 intraocular irrigating solution 0.0184% (BSS, Alcon, Inc.). As an index of gelation of hydrogel-forming materials having various concentrations, the dynamic viscoelasticity was measured immediately after mixing both solutions so that HA-DBCO and HA-AEA have the same weight. Note that to the test samples used in the measurement of the dynamic viscoelasticity, Brilliant Blue G (final concentration: 0.27 mg/mL, BBG) was added as a visualizing agent when the HA-DBCO solution and the HA-AEA solution were mixed.

(Measuring Instrument)

Rheometer: Modular Compact Rheometer MCR302 (Anton Paar)

Probe: PPT25-SN38699 [Distance between surface of sample table of rheometer and surface of probe: 0.5 mm]

Sample amount: 280 μL

Measurement temperature: 25° C.

Frequency: 1 Hz

Measurement time: 900 seconds

Interval: 1 second

Analysis software: RHEOPLUS/32 V3.62

1-3. In Vitro Evaluation of Peeling Performance

By using a triamcinolone acetonide (TA) preparation (MaQaid (registered trademark), Wakamoto Pharmaceutical Co., Ltd.), which is used as a visualizing material at the time of vitreous surgery, as a model, the peeling performance was evaluated for the hydrogel-forming materials having various concentrations.

40 mg of MaQaid (registered trademark) was suspended in BSS at 10 mg/mL, whereby a TA stock solution was obtained. BSS was dispensed into a 24-well plate at 2 mL/well. 200 μL of the TA stock solution treated with a vortex was dispensed into each well (2 mg of TA/well), whereby a TA layer was formed on the bottom face of the well. 350 μL of a mixed liquid of HA-DBCO and HA-AEA prepared by the same procedure as in the above 1-2 (5 to 10 seconds after stirring) was quickly released so as to cover the entire surface of the TA layer. After leaving for an arbitrary time to form a hydrogel, the hydrogel was removed from the well using tweezers. The TA remaining in the well was collected in a microcentrifuge tube, and the supernatant was removed by centrifugation (>9,200×g, 5 minutes). The precipitated TA was suspended in water, and the turbidity (OD 660 nm) was measured with a spectrophotometer. The turbidity of a 1 mg/mL TA/BSS suspension was used as a control, and the residual amount of TA in each well was determined. The peeling ratio was calculated from the amount of TA dispensed into the well and the residual amount of TA.

Peeling ratio (%)=(2 mg−residual amount of TA)/2 mg×100

1-4. Results

Figure 2:
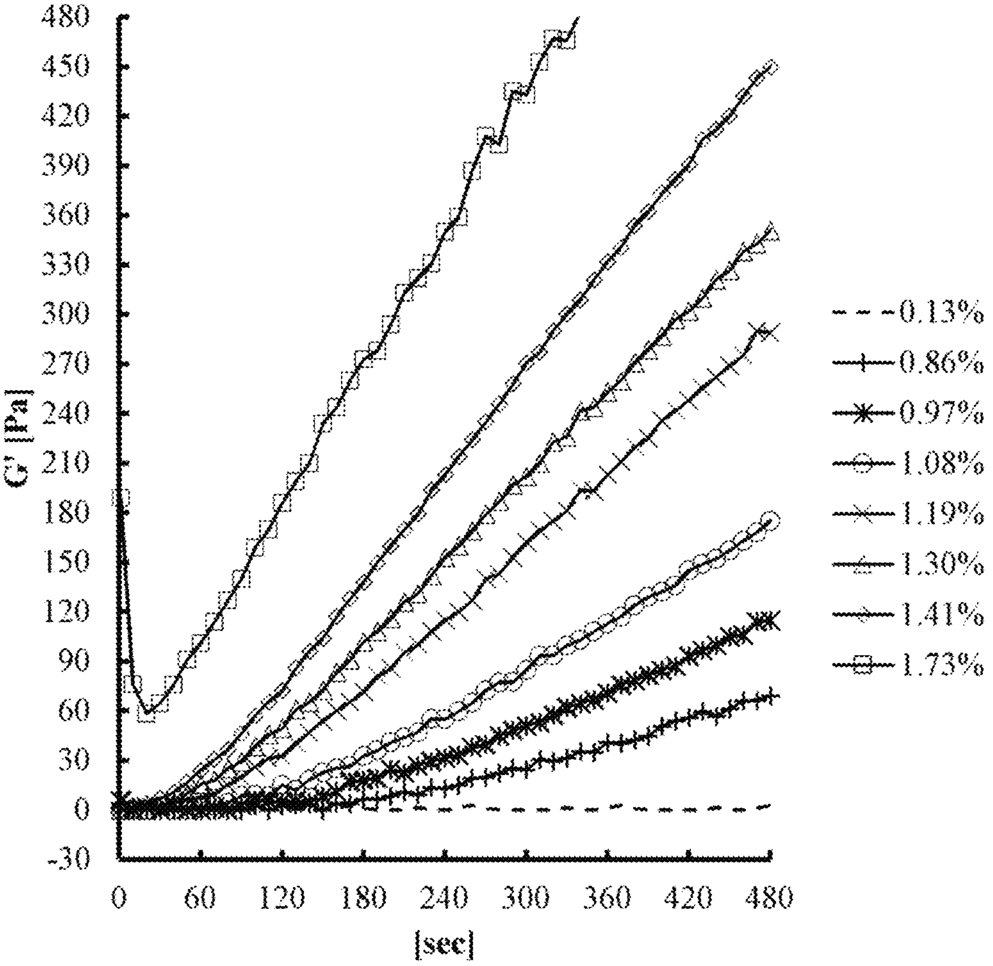
FIG. 2 is a view showing a time course of a storage elastic modulus G' after mixing HA-DBCO and HA-AEA.

The results when the indwelling time was 5 minutes are shown in FIG. 2. After mixing HA-DBCO and HA-AEA, gelation was immediately initiated. As shown in FIG. 2, the change in the storage elastic modulus of each test sample showed a sigmoid curve-like shape. From the measurement results of dynamic viscoelasticity, the maximum change rate ($V_{max}$ (Pa/sec)) of the storage elastic modulus (G' (Pa)) per unit time (sec) was calculated.

The results are shown in Table 1. The concentration of the hydrogel-forming material refers to the total amount of HA-DBCO and HA-AEA. The leaving time represents a time in which the hydrogel-forming material was placed. The detachment rate is an average value of the peeling performance evaluation performed in duplicate.

TABLE 1

| Concentration of hydrogel-forming material (wt %) | $V_{max}$ (Pa/sec) | Leaving time (min) | Peeling ratio (%) |
|---|---|---|---|
| 0.13 | 0.00 | 5 | 7 |
| 0.76 | 0.19 | 10 | 55 |
| 0.86 | 0.28 | 5 | 45 |
| 0.86 | 0.28 | 10 | 84 |
| 0.97 | 0.37 | 5 | 71 |
| 1.08 | 0.50 | 5 | 64 |
| 1.19 | 0.71 | 5 | 87 |
| 1.30 | 0.82 | 5 | 71 |
| 1.41 | 1.03 | 5 | 69 |
| 1.62 | 1.20 | 5 | 66 |
| 1.73 | 1.35 | 5 | 59 |

It was suggested that the intraocular membrane can be efficiently peeled by using the hydrogel-forming material-containing solution in which the $V_{max}$ after the initiation of gelation is 3 or less exceeding 0.

Note that the storage elastic modulus of Opegan Hi (registered trademark), which is a commercially available surgical aid for cataract surgery/intraocular lens implantation (1% sodium hyaluronate preparation), did not change over time ($V_{max}$ was 0.00 (Pa/sec)) and TA could not be removed.

Example 2

2-1. Ex Vivo Evaluation of Peeling Performance

A fresh pig's eye was cut into anterior and posterior segments at the equatorial region of the eyeball, and the vitreous body was peeled and removed carefully so that the vitreous membrane remained on the retina. 0.05 mL of Kenacort (registered trademark, 40 mg/mL TA suspension preparation, Bristol Myers Squibb) was applied onto the vitreous membrane to form a TA layer. Thereafter, 0.1 mL of an equal weight mixed liquid of HA-DBCO and HA-AEA (1.20 wt % as the total amount of HA-DBCO and HA-AEA) prepared according to the same procedure as in the above 1-2 was quickly released so as to cover the entire surface of the TA layer. After leaving for 5 minutes to form a hydrogel, the hydrogel was removed from the pig's eye using tweezers.

2-2. Results

Figure 3:
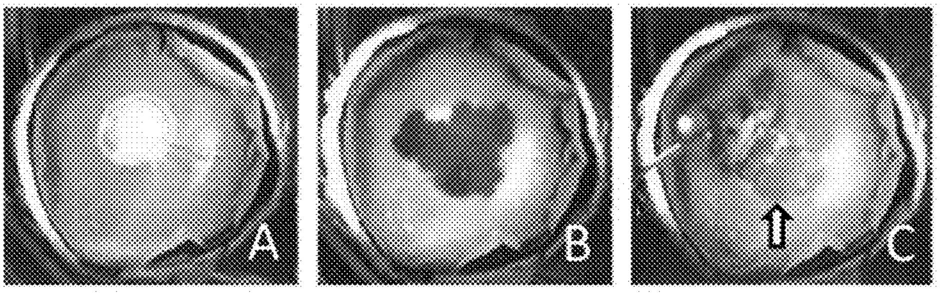
FIG. 3 is a view (drawing substitute photograph) showing the result of an evaluation of vitreous membrane peeling performance by a hydrogel in a pig's eye. A of FIG. 3 is a photograph during the formation of a TA layer, B of FIG. 3 is a photograph immediately after the release of a mixed liquid of a hydrogel-forming material, and C of FIG. 3 is a photograph during the removal operation of a hydrogel after leaving for 5 minutes.

The pig's eye during the hydrogel removal operation was observed using a stereomicroscope (magnification: 8 times) at the time of formation of the TA layer (A of FIG. 3), immediately after the release of the mixed liquid (B of FIG. 3), and after leaving for 3 minutes (C of FIG. 3). In addition, the pig's eye after removal of the hydrogel was observed with an optical microscope (magnification: 32 times, FIG. 4). In A of FIG. 3, a white portion at the central portion is the formed TA layer. In B of FIG. 3, a dark color portion at the central portion is the released mixed liquid. In C of FIG. 3 and FIG. 4, the arrows indicate the boundary where the hydrogel had been formed.

Figure 4:
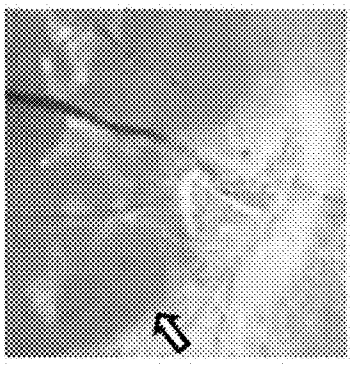
FIG. 4 is a view (drawing substitute photograph) showing the result of an evaluation of vitreous membrane peeling performance by a hydrogel in the pig's eye, and is a photograph after the hydrogel was removed.

As shown in C of FIG. 3 and FIG. 4, by removing the hydrogel, the vitreous membrane could be completely detached together with the TA layer.

Example 3

3-1. In Vivo Evaluation of Peeling Performance

The vitreous membrane peeling performance and proliferative membrane peeling performance of the hydrogel-forming material were evaluated using a rabbit. The intraocular membrane peeling surgery was performed at the Animal Center of Kyushu University and the attached operating room.

As the operating microscope used in the intraocular membrane peeling surgery, OPMI from Zeiss was used, and as the vitreous surgical instrument, ACCURUS of Alcon, Inc. was used, and was operated under the same settings as in general clinical surgery.

A posterior vitreous model animal was prepared by intravitreal injection of 0.1 mL of indoor clean air into a rabbit (adult rabbit Dutch strain, male) 2 weeks before the intraocular membrane peeling surgery.

In a proliferative vitreoretinopathy model animal, cultured pigment epithelial cells were further intravitreally injected into the posterior vitreous model animal prepared above. After the cells were injected, the rabbit was raised for 28 days, and intraocular membrane peeling surgery was performed after confirming the formation of a proliferative membrane by fundus examination.

Figure 5:
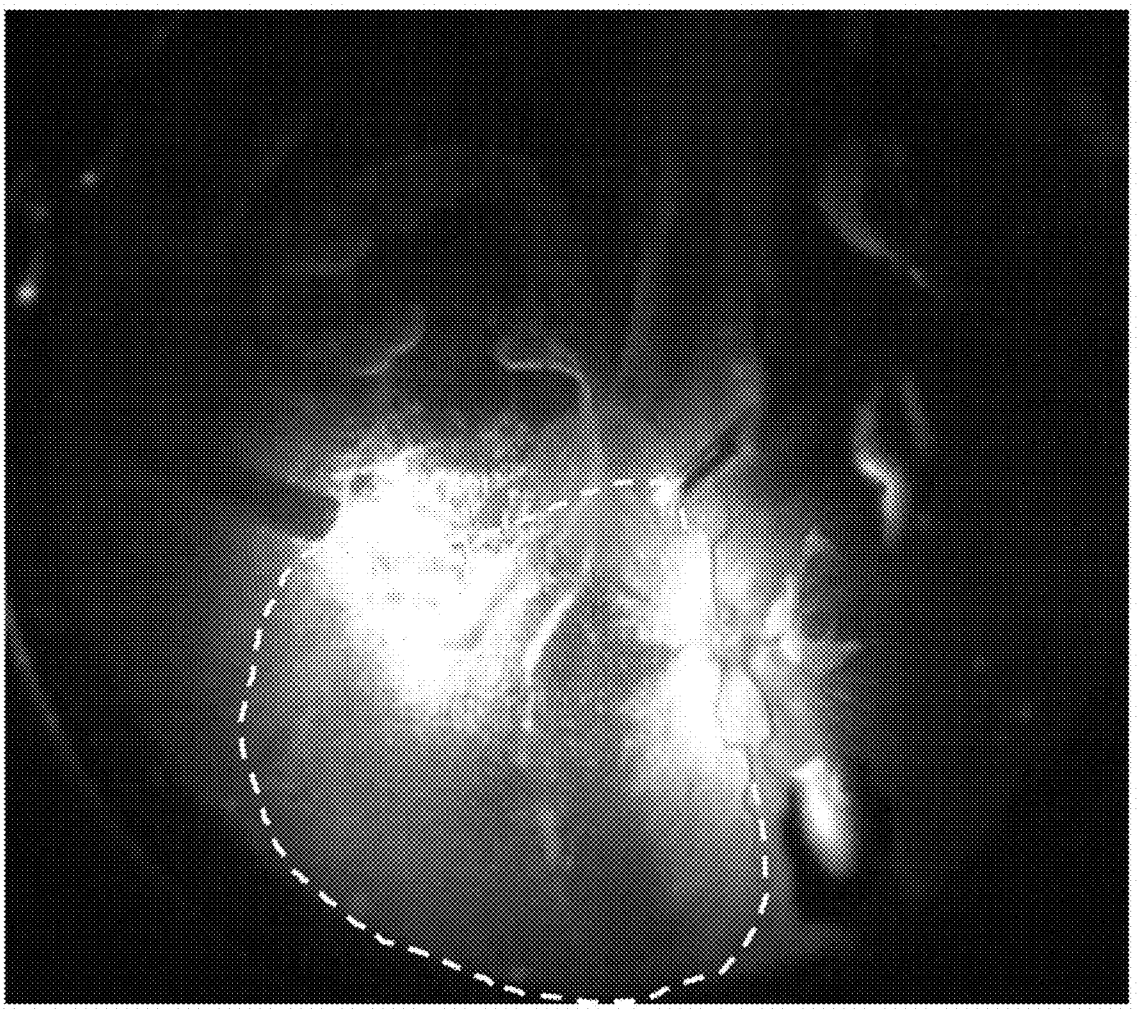
FIG. 5 is a view (drawing substitute photograph) showing the result of an evaluation of vitreous membrane and proliferative membrane peeling performance by a hydrogel in a proliferative vitreoretinopathy model animal, and is a photograph when the hydrogel was added.

In the intraocular membrane peeling surgery, four trocars were attached to the sclera. Among the four trocars, two were equipped with a chandelier lighting system, one was equipped with an irrigating system, and the remaining one was used as a port. Then, a vitrectomy was performed to expose the posterior vitreous body and the proliferative membrane (in the case of the proliferative vitreoretinopathy model animal), and thereafter, Kenacort (registered trademark) was injected into the vitreous cavity, and excess floating Kenacort was washed and aspirated. 0.1 mL of an equal weight mixed liquid of HA-DBCO and HA-AEA (1.15 wt % as the total amount of HA-DBCO and HA-AEA) prepared by the same procedure as in the above 1-2 was dropped within 30 seconds after mixing so as to cover the Kenacort using a syringe and a 27 G injection needle (FIG. 5, an area inside the dotted line is a region where the hydrogel-forming material was present). The observation was performed for 3 minutes under microscopic observation, and the posterior vitreous membrane and the proliferative membrane (in the case of a proliferative vitreous retinopathy model animal) were peeled using vitreous surgical forceps and excised using a vitreous cutter and aspirated. The eyeball after the experiment was enucleated after euthanizing the rabbit and pathologically evaluated.

3-2. Results

Figure 6:
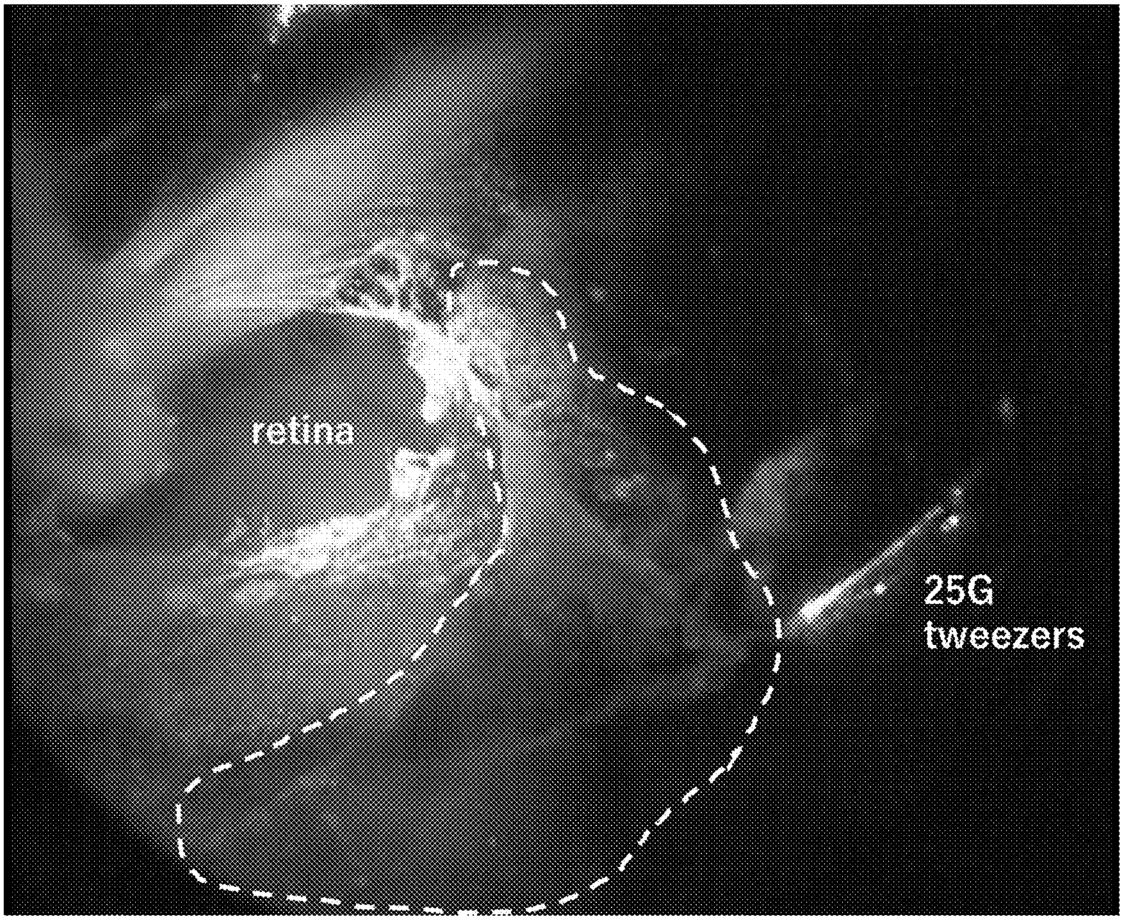
FIG. 6 is a view (drawing substitute photograph) showing the result of an evaluation of vitreous membrane and proliferative membrane peeling performance by a hydrogel in a proliferative vitreoretinopathy model animal, and is a photograph during the removal operation of the hydrogel.
Figure 7:
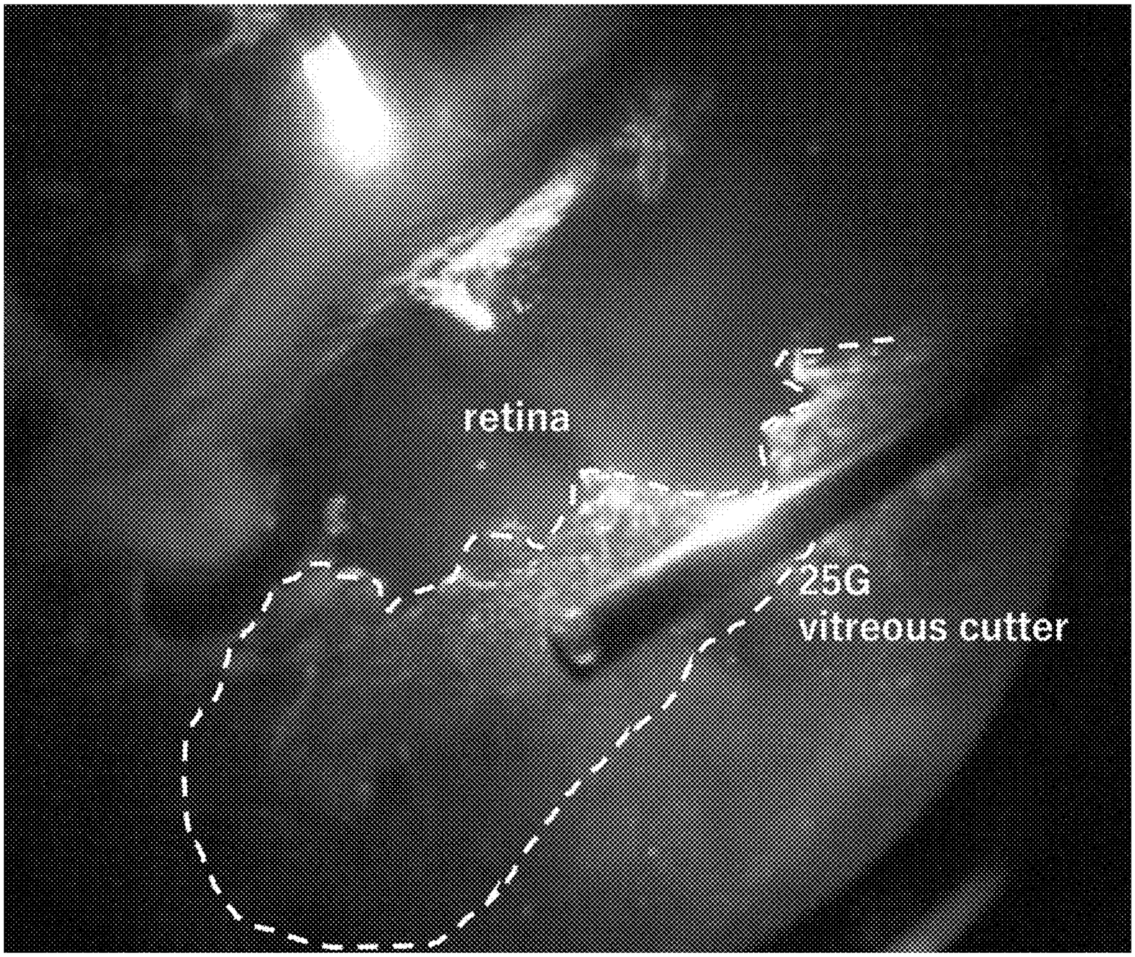
FIG. 7 is a view (drawing substitute photograph) showing the result of an evaluation of vitreous membrane and proliferative membrane peeling performance by a hydrogel in a proliferative vitreoretinopathy model animal, and is a photograph after a part of the hydrogel was removed.

The test sample injected into the rabbit's eye was transformed into a hydrogel in 3 minutes and hardened to a hardness capable of being grasped with vitreous surgical forceps. The hydrogel was gelled integrally with the posterior vitreous membrane or the proliferative membrane. When an operation was performed such that the hydrogel was grasped and peeled, the posterior vitreous membrane could be split and peeled. Similarly, the proliferative membrane could also be removed by grasping the hydrogel (FIG. 6, an area inside the dotted line is a hydrogel forming region). The peeled vitreous membrane and hydrogel can be easily excised and aspirated with a vitreous cutter, which is considered to be effective for improving the efficiency of vitreous surgery (FIG. 7, an area inside the dotted line is a hydrogel forming region).

Example 4

4-1. Safety Evaluation

The safety of the hydrogel-forming material was evaluated in vivo. As the operating microscope, OPMI of Zeiss was used. As the test sample, an equal weight mixed liquid of HA-DBCO and HA-AEA prepared according to the same procedure as in the above 3-1 was used.

At the time of surgery, a side port was prepared and the intraocular pressure was adjusted, and thereafter, 0.1 mL of the test sample was injected into the vitreous cavity using a syringe and a 27 G injection needle. Immediately after the operation, the fundus was observed to confirm the test sample. On the 1st, 3rd, 5th, and 7th days after the operation, the intraocular pressure was measured using a contact tonometer (iCare), and after checking the anterior segment of the eye, a mydriatic drug (1 drop of Mydrin-P ophthalmic solution) was instilled, and then, the fundus was observed.

4-2. Results

Corneal edema, or pathological change in the vitreous body or retina was not observed throughout the test period. The intraocular pressure showed a slight increase within the normal range on 1 to 3 days after the surgery, but was normalized by 7 days after the surgery. The test sample adhered to the vitreous body immediately after injection, but gradually swelled and dissolved, and floated in the vitreous cavity by day 5, and disappeared by day 7. After the observation period, pathological observation was performed using an optical microscope and an electron microscope, but no obvious pathological change was observed.

Example 5

5-1. Evaluation of Peeling Performance Using Commercially Available Hydrogel-Forming Material (1)

A polyethylene glycol derivative was used as a hydrogel-forming material, and its applicability as an agent for intraocular membrane peeling surgery was evaluated. In the test, a commercially available dural sealant (DuraSeal; Covidien, Inc.) packaged into a kit containing N-hydroxysuccinimide ester-polyethylene glycol (NHS-PEG) and a trilysine amine solution (crosslinking agent) was used.

Each of NHS-PEG and the crosslinking agent contained in the kit was diluted to 4 times with BSS. The diluted NHS-PEG and the diluted crosslinking agent were mixed at 1:1 (volume ratio) or 1:0.9 (volume ratio) to prepare a test sample. After mixing the diluted NHS-PEG and the diluted crosslinking agent, gelation was immediately initiated.

In accordance with the above 1-2 and 1-3, the measurement of the dynamic viscoelasticity and the in vitro evaluation of the peeling performance were performed.

5-2. Results

After mixing NHS-PEG and the crosslinking agent, gelation was immediately initiated. From the measurement results of the dynamic viscoelasticity, the maximum change rate ($V_{max}$ (Pa/sec)) of the storage elastic modulus (G' (Pa)) per unit time (sec) was calculated.

The results are shown in Table 2.

TABLE 2

| NHS-PEG : crosslinking agent (v:v) | $V_{max}$ (Pa/sec) | Leaving time (min) | Peeling ratio (%) |
|---|---|---|---|
| 1:1 | 1.48 | 5 | 85 |
| 1:0.9 | 0.33 | 5 | 82 |

It was shown that even if a polyethylene glycol derivative is used as the hydrogel-forming material, it can be applied as an agent for intraocular membrane peeling surgery by controlling the $V_{max}$ after initiating the gelation of the preparation to 3 or less exceeding 0 through dilution or adjusting the addition amount of the crosslinking agent, or the like.

On the other hand, it was shown that when the hydrogel-forming material is only a polyethylene glycol derivative, the ductility at the time of peeling is high, and a preparation containing a glycosaminoglycan derivative is superior in terms of handleability in a small intraocular space.

Example 6

6-1. Evaluation of Peeling Performance Using Commercially Available Hydrogel-Forming Material (2)

A commercially available hyaluronic acid-based scaffolding material for three-dimensional cell culture was used as a hydrogel-forming material, and its applicability as an agent for intraocular membrane peeling surgery was evaluated. In the test, a commercially available scaffolding material for three-dimensional culture (HyStem; Advanced BioMatrix) packaged into a kit containing thiol-modified hyaluronic acid (Glycosil) and thiol-reactive polyethylene glycol diacrylate (Extralink) was used.

Glycosil contained in the kit was diluted with BSS to prepare a 2 wt % Glycosil solution. In addition, Extralink was diluted with BSS to prepare an Extralink solution at 1 wt %, 2 wt %, or 3 wt %. The Extralink solution and the Glycosil solution were mixed at 1:2 (volume ratio) to prepare a test sample. After mixing the Extralink solution and the Glycosil solution, gelation was immediately initiated.

In accordance with the above 1-2, the dynamic viscoelasticity was measured. In addition, in accordance with the above 1-3, the in vitro evaluation of the peeling performance (leaving time: 5 minutes) was performed using a mixed liquid of the 3 wt % Extralink solution and the Glycosil solution as the test sample.

6-2. Results

From the measurement results of the dynamic viscoelasticity, the maximum change rate ($V_{max}$ (Pa/sec)) of the storage elastic modulus (G' (Pa)) per unit time (sec) was calculated. The results are shown in Table 3.

TABLE 3

| Concentration of Extralink solution (wt %) | Concentration of Glycosil solution (wt %) | Extralink : Glycosil (v:v) | $V_{max}$ (Pa/sec) | Peeling ratio (%) |
|---|---|---|---|---|
| 1 | 2 | 1:2 | 0.10 | — |
| 2 | | | 0.42 | — |
| 3 | | | 0.46 | 82 |

—: not performed

It was shown that the material can be applied as an agent for intraocular membrane peeling surgery by controlling the $V_{max}$ after initiating the gelation of the preparation to more than 0 and not more than 3 through dilution or adjusting the reaction equal amount, or the like.

Example 7

7-1. Measurement of Ductility

The ductility of a preparation was measured using an equal weight mixed liquid of HA-DBCO and HA-AEA (1.1 wt % as the total amount of HA-DBCO and HA-AEA, glycosaminoglycan derivative 1) prepared by the same procedure as in the above 1-2, a commercially available dural sealant diluted to 4 times described in the above 5-1 (diluted NHS-PEG:diluted crosslinking agent=1:1 (volume ratio), polyethylene glycol derivative), and the cell scaffolding material described in 6-1 (2 wt % Glycosil solution: 3 wt % Extralink solution=2:1 (volume ratio), glycosaminoglycan derivative+polyethylene glycol derivative) as the test samples.

The measurement of the ductility was performed by a compression test method according to the method of Watanabe et al. (Literature: Ippei Watanabe et al., Chem. Pharm. Bull. 67(3), 277-283 (2019)) using a texture analyzer (TA. XT plus, Stable Micro Systems, UK) equipped with a cylindrical probe made of polyoxymethylene (contact surface area: 78.5 $mm^2$). The measurement was performed at 20° C. to 25° C. Specifically, a sterile plate made of polystyrene (outer diameter: 90 mm) was fixed on a measuring table, and a test sample (0.1 mL) was dispensed in the center thereof. After leaving for 3 minutes, the probe was moved downward at 0.5 mm/sec and adhered to the test sample, and then immediately moved upward at 0.5 mm/sec for 8 seconds. A force at the time when the ductility of each test sample is teared off (the test sample itself was torn off or the test sample was detached from the contact face with the probe or the plate) was measured. The tensile stress ($N/mm^2$) was calculated by dividing the measured value by the unit area of the probe.

7-2. Results

The measurement results of the ductility are shown in Table 4.

TABLE 4

| Hydrogel-forming material | Tensile stress ($N/mm^2$) |
|---|---|
| HA-DBCO/HA-AEA | $-1.39 \times 10^{-4}$ |
| Polyethylene glycol derivative | $< -1.34 \times 10^{-3}$ |
| Glycosil/Extralink | $-0.69 \times 10^{-4}$ |

When only the polyethylene glycol derivative was used, no fracture was observed during the measurement period, and its tensile stress was less than $-1.34\times10^{-3}$ $N/mm^2$.

The tensile stress of the agent for intraocular membrane peeling surgery containing the glycosaminoglycan derivative was $-3\times10^{-4}$ $N/mm^2$ or more in each case.

It was shown that when the tensile stress 3 minutes after the initiation of gelation of the preparation was $-3\times10^{-4}$ $N/mm^2$ or more, it is particularly suitable as an agent for intraocular membrane peeling surgery.

Example 8

8-1. Preparation of Hydrogel-Forming Material

HA-DBCO (hydrogel-forming material 3) was obtained in accordance with the procedure in Example 1 except that the addition amount of the DBCO-amine solution to the HA reaction solution (60 mL) was changed to 3 mL. Further, HA-AEA (hydrogel-forming material 4) was obtained in accordance with the procedure in Example 1 except that the addition amount of the AEA solution to the HA reaction solution (60 mL) was changed to 3 mL.

The dynamic viscoelasticity was measured in accordance with the above 1-2. Further, the in vitro evaluation of the peeling performance (leaving time: 5 minutes, concentration of hydrogel-forming material=0.78 wt %) was performed in accordance with the above 1-3.

8-2. Degree of Substitution with Reactive Functional Group

By using the HA-DBCO prepared in Examples 1 and 8, the degree of substitution (DS) with the reactive functional group (cycloalkynylenyl group) per HA disaccharide unit was determined by $^1$H-NMR analysis. Specifically, about 10 mg of the HA-DBCO was dissolved in 1 mL of heavy water ($D_2O$), and the resultant was lyophilized. The lyophilized powder was reconstituted in 0.7 mL of $D_2O$, and the resultant was transferred to an NMR tube. $^1$H-NMR data were acquired using an NMR device (Bruker AVANCE III 500, 500 MHz type) and the data were analyzed. In the $^1$H-NMR analysis of HA-DBCO, a chemical shift derived from an aromatic proton, which is a partial structure of the cycloalkynylenyl group, was detected at 7-8 ppm.

For the HA-AEA prepared in Examples 1 and 8, the degree of substitution (DS) with the reactive functional group (azide group) per hyaluronic acid disaccharide unit was determined by the following procedure. Specifically, the AEA residue of the HA-AEA was converted into the following structure (in the following structure, * indicates a binding site with an ethylene group) by subjecting the HA-AEA and an excess amount of the DBCO-Amine to a click reaction. For the product by the click reaction, $^1$H-NMR data was acquired in the same manner as in the case of the HA-DBCO. In the $^1$H-NMR analysis thereof, a chemical shift derived from an aromatic proton was detected at 7-8 ppm.

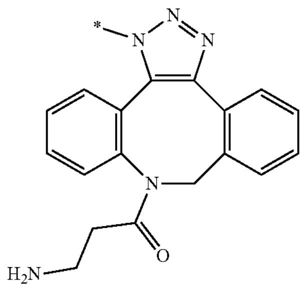 [SMILES: *n1nnc2c1-c1ccccc1N(C(=O)CCN)Cc1ccccc1-2]

DS (a value expressing the number of substituents with respect to the number of hyaluronic acid disaccharide repeating units as a percentage) was determined by calculating the ratio of the relative peak area (integral value) of the aromatic proton and the proton (1.9 to 2.1 ppm) derived from an N-acetyl group, which is a partial structure of hyaluronic acid disaccharide (the following formulae 3 to 5). Note that 8 as the number of aromatic protons in the formula 3, and 3 as the number of N-acetyl group-derived protons in the formula 4 were used as the constant. The results are shown in Table 5.

Value $A$=[Addition value of each peak area of aromatic protons]/[Number of aromatic protons] (Formula 3)

Value $B$=[Addition value of peak area of N-acetyl group-derived protons]/[Number of N-acetyl group-derived protons] (Formula 4)

$DS[\%]=(\text{value } A/\text{value } B)\times100$ (Formula 5)

TABLE 5

| | Reactive functional group | DS (%) |
|---|---|---|
| Hydrogel-forming material 1 | cycloalkynylenyl group | 9 |
| Hydrogel-forming material 2 | azide group | 9 |
| Hydrogel-forming material 3 | cycloalkynylenyl group | 29 |
| Hydrogel-forming material 4 | azide group | 30 |

8-3. Results

After mixing the HA-DBCO and the HA-AEA, gelation was immediately initiated. ($V_{max}$ was 0.70 (Pa/sec), detachment ratio was 79%). From the above results, it was shown that by increasing the degree of substitution with the reactive functional group, even if the concentration of the hydrogel-forming material is low, $V_{max}$ can be increased.

Example 9

9-1. Evaluation of Peeling Performance Using Commercially Available Hydrogel-Forming Material (3)

A commercially available fibrinogen preparation (fibrin glue) was diluted and used as a hydrogel-forming material, and its applicability as an agent for intraocular membrane peeling surgery was evaluated. In the test, a commercially available plasma fraction preparation (Beriplast P Combi-Set Tissue adhesion; CSL Behring LLC) packaged into a kit containing fibrinogen and thrombin was used.

The measurement of the dynamic viscoelasticity and ductility was performed in accordance with the above 1-2 and 7-1.

TA layers were formed on the bottom face of wells of a 24-well plate in accordance with the above 1-3. Each of the fibrinogen-containing liquid (combination A) and the thrombin-containing liquid (combination B) contained in the kit was diluted to 10 times with BSS. A mixed liquid of 175 μL of the diluted fibrinogen-containing liquid and 10 μL of the BBG solution (10 mg/mL) was layered on the TA layer. Thereafter, 175 μL of the diluted thrombin-containing liquid was further layered thereon. After the diluted thrombin-containing liquid was layered on the diluted fibrinogen-containing liquid, gelation was immediately initiated. The peeling ratio after leaving for 5 minutes was determined in accordance with the above 1-3.

9-2. Results

From the measurement results of the dynamic viscoelasticity, the maximum change rate ($V_{max}$ (Pa/sec)) of the storage elastic modulus (G' (Pa)) per unit time (sec) was calculated. Further, from the measurement results of the ductility, the tensile stress ($N/mm^2$) was calculated.

The results are shown in Table 6.

TABLE 6

| $V_{max}$ (Pa/sec) | Tensile stress ($N/mm^2$) | Peeling ratio (%) |
|---|---|---|
| 0.02 | $-2.89 \times 10^{-4}$ | 97 |

As described above, it was shown that the material can be applied as an agent for intraocular membrane peeling surgery.

INDUSTRIAL APPLICABILITY

The agent for use in intraocular membrane peeling surgery and the method for peeling the intraocular membrane of the present invention can easily and efficiently peel the intraocular membrane, and therefore are useful as an agent for peeling the intraocular membrane in vitreoretinal surgery or the like.

Although the present invention has been described in connection with specific Examples and various embodiments, many modifications and applications of the embodiments described herein may be made without departing from the spirit and scope of the invention as will be readily understood by a person skilled in the art.

The invention claimed is:

1. A method for peeling an intraocular membrane, comprising applying an agent comprising a solution comprising a hydrogel-forming material onto an intraocular membrane of a patient, and peeling the intraocular membrane together with a hydrogel adhered to the intraocular membrane, wherein the agent satisfies the following formula 1 with respect to the dynamic viscoelasticity measured at a temperature of 25 to 40° C. and a frequency of 1 Hz:

$$0 < V_{max} \leq 3, \quad \text{(Formula 1)}$$

wherein $V_{max}$ (Pa/sec) is the maximum change rate of the storage elastic modulus after the initiation of gelation, wherein the hydrogel-forming material comprises two or more types of compounds, and wherein the gelation is caused by a crosslinking reaction initiated by mixing the two or more types of compounds.

2. The method according to claim 1, wherein the intraocular membrane is peeled after 10 seconds or more have elapsed from the intraocular administration.

3. The method according to claim 1, wherein the hydrogel-forming material comprises a polymer.

4. The method according to claim 2, wherein the polymer comprises a compound selected from the group consisting of a polysaccharide derivative, a polyalkylene glycol derivative, a collagen derivative, a polyvinyl alcohol derivative, and fibrinogen.

5. The method according to claim 1, wherein the intraocular membrane is at least one selected from the group consisting of a vitreous membrane and a proliferative membrane.

6. The method according to claim 1, wherein a tensile stress measured using a texture analyzer 3 minutes after the initiation of gelation is $-3\times10^{-4}$ $N/mm^2$ or more.

7. The method according to claim 1, wherein the agent comprises a visualizing agent.

8. The method according to claim 1, wherein the agent satisfies the following formula 2 with respect to the dynamic viscoelasticity measured at a temperature of 25 to 40° C. and a frequency of 1 Hz:

$$0.05 \leq V_{max} \leq 2, \quad \text{(Formula 2)}$$

wherein $V_{max}$ (Pa/sec) is the same as in the formula 1.

9. The method according to claim 1, wherein $V_{max}$ is the maximum change rate of the storage elastic modulus after the initiation of gelation until 900 seconds.

10. The method according to claim 1, wherein the hydrogel-forming material comprises the following glycosaminoglycan derivative A and one selected from the group consisting of the following glycosaminoglycan derivative B and compound C:

(1) a glycosaminoglycan derivative A in which an SPAAC-type reactive group is introduced into a carboxyl group of a glycosaminoglycan via an amide bond and a divalent spacer group;

(2) a glycosaminoglycan derivative B in which a complementary reactive group to the reactive group in (1) is introduced into a carboxyl group via an amide bond and a divalent spacer group; and (3) a compound C defined by the following structure having at least two complementary reactive groups to the reactive group in (1):

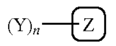

wherein Y' are the same or different and are each a complementary reactive group to the reactive group in (1); Z is an n-valent spacer group; and n is an integer of 2 or more.

11. The method according to claim 1, wherein the agent is filled in an injector.

12. A method for peeling an intraocular membrane, comprising injecting a solution comprising a hydrogel-forming material into an eye of a patient to form a crosslinked hydrogel adhered to the intraocular membrane, and peeling the intraocular membrane together with the hydrogel.

13. The method according to claim 12, wherein the hydrogel-forming material comprises a polymer.

14. The method according to claim 13, wherein the polymer comprises a compound selected from the group consisting of a polysaccharide derivative, a polyalkylene glycol derivative, a collagen derivative, a polyvinyl alcohol derivative, and fibrinogen.

15. The method according to claim 12, wherein the intraocular membrane is at least one selected from the group consisting of a vitreous membrane and a proliferative membrane.

16. The method according to claim 12, wherein the solution comprises a visualizing agent.

17. The method according to claim 12, wherein the hydrogel-forming material comprises the following glycosaminoglycan derivative A and one selected from the group consisting of the following glycosaminoglycan derivative B and compound C:

(1) a glycosaminoglycan derivative A in which an SPAAC-type reactive group is introduced into a carboxyl group of a glycosaminoglycan via an amide bond and a divalent spacer group;

(2) a glycosaminoglycan derivative B in which a complementary reactive group to the reactive group in (1) is introduced into a carboxyl group via an amide bond and a divalent spacer group; and (3) a compound C defined by the following structure having at least two complementary reactive groups to the reactive group in (1):

wherein Y' are the same or different and are each a complementary reactive group to the reactive group in (1); Z is an n-valent spacer group; and n is an integer of 2 or more.

18. The method according to claim 12, wherein the solution is filled in an injector.

19. The method according to claim 12, wherein the intraocular membrane is peeled after 10 seconds or more have elapsed from the intraocular injection.

* * * * *